United States Patent [19]
Nachbar

[11] Patent Number: 5,146,786
[45] Date of Patent: Sep. 15, 1992

[54] ROTARY UNION FOR USE WITH ULTRASONIC THICKNESS MEASURING PROBE

[75] Inventor: Henry D. Nachbar, Schenectady, N.Y.

[73] Assignee: The United States of America as represented by the United States Department of Energy, Washington, D.C.

[21] Appl. No.: 660,183

[22] Filed: Feb. 7, 1991

[51] Int. Cl.$^5$ .......................................... G01N 29/26
[52] U.S. Cl. ........................................ 73/623; 73/644
[58] Field of Search .................... 73/644, 623, 632; 310/336

[56] References Cited

U.S. PATENT DOCUMENTS

| | | | |
|---|---|---|---|
| 3,584,504 | 6/1971 | Proctor et al. | 73/623 |
| 4,102,206 | 7/1978 | Perdijon | 73/644 |
| 4,981,044 | 1/1991 | Adams et al. | 73/623 |
| 5,025,215 | 6/1991 | Pirl | 73/623 |
| 5,046,364 | 9/1991 | Stasuk et al. | 73/623 |

Primary Examiner—Hezron E. Williams
Assistant Examiner—Rose M. Finley
Attorney, Agent, or Firm—Virginia B. Caress; William R. Moser; Richard E. Constant

[57] ABSTRACT

A rotary union for rotatably supporting an ultrasonic probe operable to nondestructively measure the thickness of steam generator tubes to determine the amount of corrosion experienced by the tubes includes a stationary body having a bore therethrough and an outlet drain, and a fitting rotatably mounted within the upper end of the body. The fitting has a bore aligned with the bore of the body. An electrical cable positioned within a water supply tube in an annular arrangement passes through the bore of the body and the bore of the fitting. This annular arrangement, in turn, is positioned within a connector element which extends outwardly from the fitting bore and is connected to the ultrasonic probe. An elastomeric lower bushing seals the annular arrangement to the lower end of the rotary union body and an elastomeric upper bushing seals the connector element to the fitting to permit the connector element and the ultrasonic probe connected thereto to rotate with the fitting relative to the body. The lower and upper bushings permit water to be passed through the annular arrangement and into the ultrasonic probe and thereafter discharged between the annular arrangement and the connector element to the outlet drain of the rotary union body.

14 Claims, 2 Drawing Sheets

ROTARY UNION FOR USE WITH ULTRASONIC THICKNESS MEASURING PROBE

RIGHTS OF THE GOVERNMENT

The United States Government has rights in this invention pursuant to Contract No. DE-AC12-76SN00052 awarded by the U. S. Department of Energy to General Electric Corporation.

CROSS-REFERENCE TO RELATED APPLICATIONS

Reference is hereby made to the following copending application dealing with related subject matter and assigned to the assignee of the present invention: "Ultrasonic Thickness Measuring and Imaging System and Method" by P. J. Bylenok et al, assigned, U.S. Ser. No. 07/565,524 and filed Aug. 10, 1990, still pending.

BACKGROUND OF THE INVENTION

1. Field of the Invention

The present invention relates generally to corrosion testing of steam generator tubes and, more particularly, to a rotary union for rotatably supporting an ultrasonic probe operable to nondestructively determine the amount of corrosion experienced by the tubes.

2. Description of the Prior Art

Heat produced by fission in a nuclear reactor core of a nuclear power plant is transferred to a primary reactor coolant flowing through the reactor core. The primary reactor coolant then flows through steam generators of the nuclear power plant where it transfers the heat to a secondary feedwater which is transformed thereby into steam. The steam is used to generate electricity by driving a conventional steam turbine-electrical generator apparatus.

Each steam generator has a large bundle of tubes. The high temperature primary reactor coolant flows through the interior of the tubes in heat exchange relationship with the feedwater flowing along the exterior of the tubes. The primary reactor coolant flowing through the steam generator tubes is a source of corrosion of the walls of the tubes which reduces wall thickness and can eventually lead to wall perforations.

As a result, long term corrosion tests of steam generator tubes are conducted in order to understand the corrosion generating mechanism and to determine typical steam generator tube corrosion rates.

One type of test performed to determine the amount of corrosion experienced by a steam generator tube is a nondestructive test which utilizes an ultrasonic probe placed inside the tube. The tube is filled with water to allow an ultrasonic wave generated by the probe to travel from the probe through the water and into the tube wall. The reflected ultrasonic wave is monitored by the same probe. The time required for the ultrasonic wave to complete a round trip in the tube wall is proportional to the tube wall thickness. The relationship between wave travel time and tube thickness is:

$$T = (vt)/2$$

where:
T = tube wall thickness (inches)
v = velocity of ultrasound in metal
t = travel time (micro-seconds).

If it is desired to nondestructively determine the amount of corrosion which has occurred over a selected section of a steam generator tube, the ultrasonic probe must be passed through the inside of the tube over the section being tested. In addition, in order to determine the amount of corrosion which has occurred around a selected circumference of the tube, the ultrasonic probe must be rotated in a complete circle. Since the tube is positioned vertically within the steam generator shell, the ultrasonic probe must be introduced into the bottom of the tube which terminates at the open lower end portion of the steam generator shell and thereafter extended upwardly into the interior of the tube and rotated in sweeping fashion to nondestructively determine the amount of corrosion which has occurred over the entire section of tube.

In practice, the ultrasonic probe utilized to nondestructively determine the amount of corrosion experienced by a steam generator tube has heretofore been supported by an adaptor which has a hollow interior through which passes both an electrical cable for providing an electrical signal to the ultrasonic probe and water to be utilized by the probe. The adaptor itself is maintained in position within the open lower end portion of the steam generator adjacent to the bottom of the tube to be tested. A connector element in the form of a hollow pipe is used to secure the ultrasonic probe to the adaptor and also acts as a conduit for the electrical cable and water supplied to the probe. In order to extend the ultrasonic probe upwardly into the interior of the tube under test, additional sections of pipe are interposed between the ultrasonic probe and the adaptor.

Although this adaptor has been used in the past to support the ultrasonic probe, its use has caused problems for operating personnel. Since the adaptor itself is a rigid assembly, the entire adaptor must be rotated in order to allow the ultrasonic probe to sweep the entire inside circumference of the tube. It has been found that this rigid adaptor, due to its construction, interferes with the steam generator open end portion outer shell, particularly during ultrasonic inspection of the outer ring of steam generator tubes. In addition, if it is desired to add additional sections of pipe between the ultrasonic probe and the adaptor to extend the probe upwardly into the tube, the water supply to the probe must be disconnected and the electrical cable disconnected from its electrical signal supply and pulled out of the adaptor. Only after the additional sections of pipe are added can the water supply to the probe be reconnected and the electrical cable be reinserted through the pipes and adaptor to be reconnected to the electrical signal supply. It is apparent that this requirement of having to continually disconnect and then reconnect the electrical signal and water supplies from the ultrasonic probe in order to add sections of pipe between the probe and adaptor to extend the probe upwardly into the interior of the tube under test greatly increases overall tube inspection time and the amount of work required to be performed by test personnel.

Consequently, a need exists for an improved adaptor in the form of a rotary union for supporting an ultrasonic probe which is capable of accepting sections of pipe to extend the probe upwardly into the tube under test without requiring the water and electrical signal supplies to the probe to be disconnected. Utilizing a rotary union to support the ultrasonic probe will also provide the added benefit of permitting the ultrasonic probe to be rotated while the body of the union remains stationary in order to eliminate the steam generator interference problems experienced by the adaptor presently used.

SUMMARY OF THE INVENTION

The present invention provides a rotary union for supporting an ultrasonic probe designed to satisfy the aforementioned needs. The rotary union of the present invention is capable of supporting an ultrasonic probe for rotary movement relative to the union and also permits the ultrasonic probe to be extended upwardly into the steam generator tube under test without requiring the probe to be repeatedly disconnected from it source of water and electrical signals.

In accordance with the present invention, the rotary union includes a stationary body having a lower end portion, an opposite upper end portion, a bore extending through the body from the lower end portion to the upper end portion and an outlet drain extending between the bore and the outer side wall of the body. A rotatable fitting is rotatably mounted within the upper end portion of the body and has a bore extending therethrough which is aligned with the bore of the body. The bore of the fitting and the bore of the body are aligned to permit an annular arrangement which includes an electrical cable positioned within a water supply tube and a connector element surrounding the annular arrangement to pass through the bore of the body and the bore of the fitting. The electrical cable and water supply tube provide electrical signals and water, respectively, to an ultrasonic probe connected to the connector element.

The rotary union further includes lower sealing means in the form of an elastomeric bushing for sealing the annular arrangement to the lower end of the body, and upper sealing means in the form of a bushing for sealing the connector element to the fitting and permitting the connector element and the ultrasonic probe connected thereto to rotate with the fitting relative to the body of the union. The lower and upper sealing means permit water to be introduced through the annular arrangement for operation of the ultrasonic probe and thereafter discharged between the annular arrangement and the connector element to the outlet drain of the union body.

These and other advantages and attainments of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which.

DETAILED DESCRIPTION OF THE INVENTION

Figure 1:
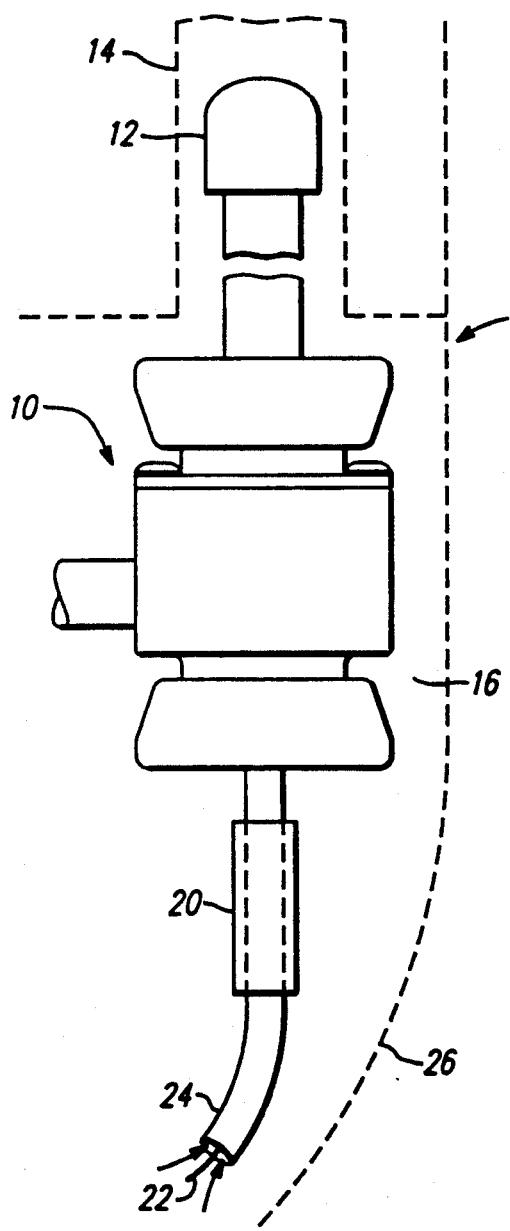
FIG. 1 is a view in side elevation of the rotary union of the present invention located within the open lower end portion of a steam generator shell and supporting an ultrasonic probe positioned within a steam generator tube illustrated in phantom.

In the following description, like reference characters designate like or corresponding parts throughout the several views of the drawings. Also in the following description, it is to be understood that such terms as "forward", "rearward", "left", "right", "upwardly", "downwardly", and the like are words of convenience and are not to be construed as limiting terms.

Referring now to the drawings, and particularly to FIG. 1, there is shown a rotary union 10 which is the subject of the present invention for rotatably supporting an ultrasonic probe 12 operable to nondestructively determine the amount of corrosion experienced by a steam generator tube 14 illustrated in phantom. The rotary union 10 is positioned in the open lower end portion 16 of a steam generator 18. As will be explained herein, the rotary union 10 has a construction to rotatably support a connector element 20 which is connected to the ultrasonic probe 12 to extend the probe into the interior of the tube 18, and also has a construction to allow an electrical cable 22 and a water supply tube 24 which respectively supply electrical signals and water to the probe 12 to pass through the interior of the union 10. In addition, the construction of the rotary union 10 allows the ultrasonic probe 12 to be rotated in sweeping fashion to ultrasonically inspect the entire area of the tube 14 without the rotary union 10 interfering with the lower side wall 26 of the steam generator 18.

Figure 2:
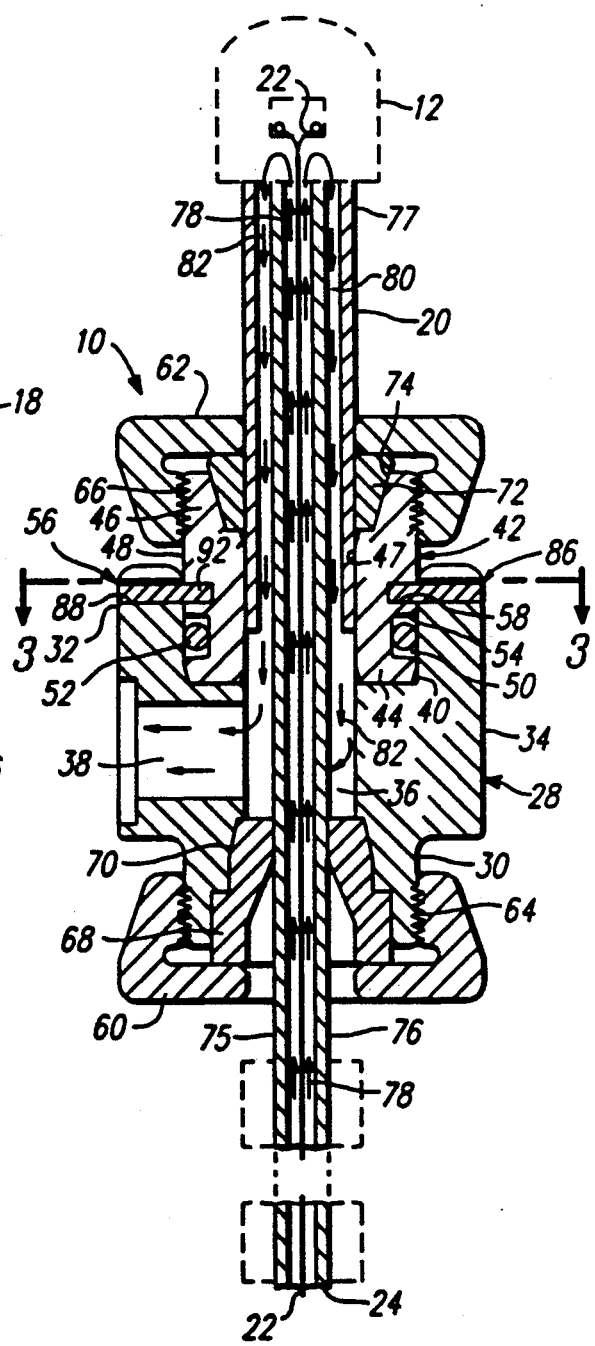
FIG. 2 is a sectional view in side elevation of the rotary union of FIG. 1, illustrating in section an electrical cable and water supply tube which pass through the union to the ultrasonic probe and a connector element extending from the union for supporting the probe.

Referring now to FIG. 2, there is illustrated a sectional view in side elevation of the rotary union 10 and the electrical cable 22, water supply tube 24 and connector element 20 positioned within the interior of the rotary union 10. The rotary union 10 includes a stationary body 28 having a lower end portion 30 and an opposite upper end portion 32. The body 28 has a generally cylindrical outer side wall 34 and a bore 36 which extends between the lower and upper end portions 30, 32 of the body 28. An outlet drain 38 extends between the bore 36 of the body 28 and the body cylindrical outer side wall 34. As will be explained later in greater detail, the outlet drain 38 provides a discharge from the rotary union 10 for water passed through the water supply tube 24 to the ultrasonic probe 12 and thereafter discharged from the probe 12.

The body 28 of the rotary union 10 includes a cylindrical recess 40 formed in its upper end portion 32. The cylindrical recess 40 is adapted to receive a fitting 42 having a lower end portion 44 positioned within the recess and an opposite upper end portion 46 extending upwardly from the body 28. The fitting 42 has a bore 47 which is aligned with the bore 36 formed in the body 28. The fitting 42 has a cylindrical side wall 48 with a circumferential O-ring groove 50 extending around the side wall 48. An O-ring 52 is positioned within the O-ring groove 50 to provide a water tight seal between the cylindrical side wall 48 of the fitting 42 and the inner wall 54 of the cylindrical recess 40.

A retaining means, generally designated by the numeral 56, is secured to the upper end portion 32 of the body 28, and a portion of the retaining means 56 extends into a groove 58 which extends around the circumference of the fitting 42 cylindrical side wall 48. The retaining means 56, which will be described in greater detail in FIG. 3, captures the fitting 42 within the cylindrical recess 40 while at the same time allows the fitting 42 to rotate relative to the body 28 of the rotary union 10.

As seen in FIG. 2, the rotary union 10 further includes a lower cap 60 and an upper cap 62. The lower cap 60 is releasably secured to threads formed on the lower end portion 30 of the body 28 via mating threads formed on the inner wall 64 of the cap 60. The upper cap 62 is releasably secured to threads formed on the upper end portion 46 of the fitting 42 via mating threads formed on the inner wall 66 of the cap 62. When engaged with the threads formed on the lower end portion 30 of the body 28, the lower cap 60 operates to urge an elastomeric bushing 68 preferably made of rubber into a counterbore 70 formed in the lower end portion 30 of the body 28. As the bushing 68 is urged into the counterbore 70, it is forced against the outer side wall 75 of the annular arrangement 76 defined by the electrical cable 22 positioned within the water supply tube 24. In like fashion, the upper cap 62 operates to urge an elastomeric bushing 72 also preferably made of rubber into a counterbore 74 formed in the upper end portion 46 of the fitting 42 when the cap 62 is engaged with the threads formed on the upper end portion 46 of the fitting 42. As the bushing 72 is urged into the counterbore 74, it is forced against the outer side wall 77 of the connector element 20 extending outwardly from the fitting 42.

This "urging" action of the lower bushing 68 against the outer side wall 75 of the annular arrangement 76 and the upper bushing 72 against the outer side wall 77 of the connector element 20 causes the annular arrangement 76 to be sealed to the lower end portion 30 of the body 28 and the connector element 20 to be sealed to the upper end portion 46 of the fitting 42.

With the annular arrangement 76 and connector element 20 sealed to the body 28 and fitting 42, respectively, water may be passed through the rotary union 10 to the ultrasonic probe 12 and thereafter discharged in the following manner. Water delivered from a source (not shown) is introduced into the annular arrangement 76 to follow the electrical cable 22 upwardly through the water supply tube 24 towards the ultrasonic probe in a direction indicated by the arrows 78. The water is thereafter introduced into the ultrasonic probe 12, and discharged from the probe 12 into the area 80 between the water supply tube 24 and the connector element 20. The water discharged into the area 80 flows downwardly in a direction indicated by the arrows 82 and into the bore 36 of the body 28. Water entering the bore 36 of the body 28 cannot leak from the union 10 between the bushing 68 and the outer side wall 75 of the annular arrangement 76 since the bushing 68 is sealed to the side wall 75 by the urging action of the cap 60. Similarly, water entering the bore 36 of the body 28 cannot leak from the union 10 between the bushing 72 and the outer side wall 77 of the connector element 20 since the bushing 72 is sealed to the side wall 77 by the urging action of the cap 62. Since the sealing action of the bushings 68, 72 prevents water from leaking from the union 10, all the water which passes through the ultrasonic probe 12 and enters the bore 36 of the body 28 is forced to exit the body via the outlet drain 38.

Figure 3:
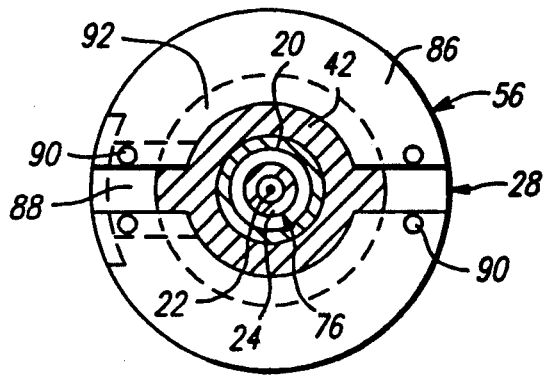
FIG. 3 is a partial sectional view of the rotary union of the present invention taken along line 3—3 of FIG. 2.

Now referring to FIG. 3, there is shown in detail the retaining means 56 utilized to maintain the fitting 42 rotatably secured within the cylindrical recess 40 formed in the upper end portion 32 of the body 28. As seen in FIG. 3, the retaining means 56 includes a pair of arcuate plates 86 which extend around the upper edge surface 88 of the body 28 and are secured to the upper edge surface 88 via screws (not shown in FIG. 3) which pass through the holes 90 formed in the plates 86. Each of the arcuate plates 86 includes an inside arcuate edge portion 92 which, as can be seen in FIG. 2, extends into the circumferential groove 58 formed in the side wall 48 of the fitting 42. The inside arcuate edge portions 92 of the arcuate plates 86 capture the fitting 42 within the cylindrical recess 40 of the body while allowing the fitting 42 to rotate within the recess 40 relative to the body 28.

Figure 4:
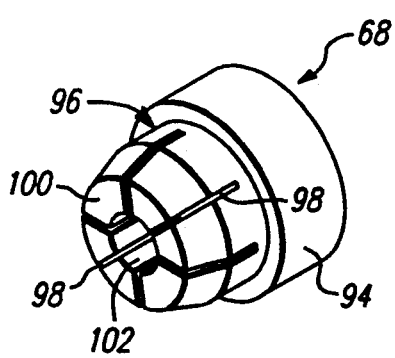
FIG. 4 is a perspective view of a split bushing forming a portion of the rotary union of the present invention which is utilized to seal the ultrasonic probe water supply tube to the lower end portion of the rotary union body.

Now referring to FIG. 4, there is shown a perspective view of the lower bushing 68 of FIG. 3. The bushing 68 is made from an elastomeric material, preferably rubber, and includes an annular base portion 94 and an annular body portion 96 extending from the base portion 94. The body portion 96 of the bushing 68 is split at a plurality of locations 98 to define a plurality of fingers 100. As will be explained with respect to FIG. 5, the fingers 100 are adapted to flex to allow a connector element to be passed through the opening 102 formed in the bushing 68.

Figure 5:
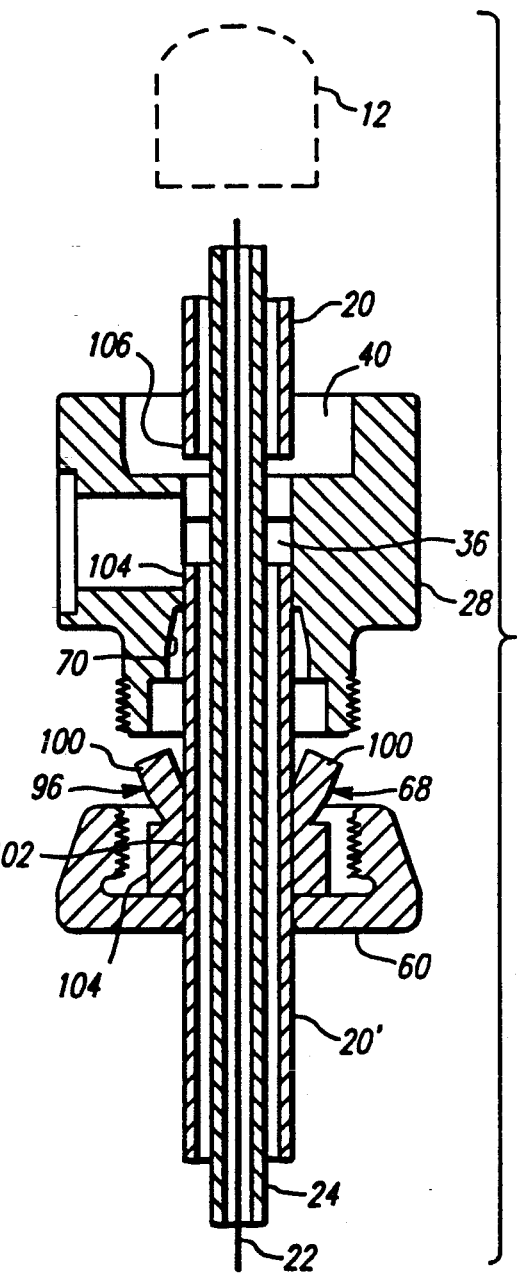
FIG. 5 is a sectional view in side elevation of the body of the rotary union of the present invention, illustrating the bushing of FIG. 4 spaced from the body of the rotary union and expanded as a connector element is passed therethrough.

Now referring to FIG. 5, there is shown a sectional view in side elevation of the body 28, lower cap 60 and bushing 68 previously described. FIG. 5 illustrates a connector element 20' in the process of being passed through the bushing 68 and into the bore 36 of the body 28 to be joined with the connector element 20. After the connector element 20' and the connector element 20 are joined at their respective adjacent facing end portions 104, 106, they may be moved together upwardly relative to the body 36 of the union 10 until the connector element 20 is moved completely out of the union 10 and a portion of the connector element 20' is positioned within the bore 47 of the fitting 42 (fitting 42 not shown in FIG. 5). In this manner, the ultrasonic probe 12, illustrated in phantom, may be moved from a first position spaced a first preselected distance from the rotary union 10 to a second position spaced a second and greater preselected distance from the rotary union 10, for example, to extend the ultrasonic probe 12 upwardly into a steam generator tube 14, such as illustrated in FIG. 1, in order to measure the thickness of the steam generator tube 14 over the distance between the first and second positions of the ultrasonic probe 12.

In order to insert the connector element 20' into the bore 36 of the body 28, the lower cap 60 is disconnected from the threaded area of the lower end portion 30 of the body 28 to release the bushing 68 from the counterbore 70 formed in the body 28. With the cap 60 and bushing 68 in position relative to the body 28 as shown in FIG. 5, the end portion 104 of the connector element 20' is started through the bushing 68. Since the portion of the opening 102 in the base portion 104 of the bushing 68 has substantially the same diameter as the diameter of the connector element 20', the connector element 20' passes freely through the base portion 102 of the bushing 68. However, the portion of the opening 102 extending through the body portion 96 of the bushing 68 is reduced in diameter and thus prevents free passage of the connector element 20' through the body portion 96. As the connector element 20' is urged through the body portion 96 of the bushing 68, the fingers 100 formed in the body portion 96 flex or expand outwardly, as illustrated in FIG. 5, to allow the connector element 20' to enter the bore 36 of the body 28 to be joined with the connector element 20.

It is thought that the present invention and many of its attendant advantages will be understood from the foregoing description and it will be apparent that various changes may be made in the form, construction and arrangement without departing from the spirit and scope of the invention or sacrificing all of its material advantages, the form hereinbefore described being merely a preferred or exemplary embodiment thereof.

I claim:

1. A rotary union for use with an ultrasonic probe which utilizes electricity and water for operation supplied by an electrical cable within a water supply tube in defining an annular arrangement positioned within a connector element connected to said ultrasonic probe and adapted to be extended from within said union, said rotary union comprising:
   (a) a stationary body having a lower end portion, an opposite upper end portion, a bore extending through said body from said lower to said upper end portions and an outlet drain extending between said bore and an outer side wall of said body for draining water utilized by said ultrasonic probe;
   (b) a rotatable fitting rotatably mounted within the upper end portion of said body and having a bore extending therethrough and aligned with said bore of said body to thereby permit said annular arrangement and said connector element to pass through said body and said fitting bore;
   (c) lower sealing means for sealing said annular arrangement to said lower end portion of said body; and
   (d) upper sealing means for sealing said connector element to said fitting and permitting said connector element and said ultrasonic probe connected thereto to rotate with said fitting relative to said body;
   said lower and upper sealing means permitting water to be introduced through said annular arrangement for operation of said ultrasonic probe and thereafter discharged between said annular arrangement and said connector element to said outlet drain.

2. The rotary union as recited in claim 1, wherein:
   a portion of said connector element is positioned within said fitting bore and the remainder of said connector element extends upwardly from said fitting to provide that said ultrasonic probe is spaced a first preselected distance from said fitting.

3. The rotary union as recited in claim 2, wherein said lower and upper sealing means are adapted to be releasably connected with said body lower end portion and said fitting respectively.

4. The rotary union as recited in claim 3, wherein another connector element may be introduced into said body bore and secured to said connector element and thereafter advanced into said fitting bore to push said connector element out of said fitting to thereby space said ultrasonic probe a second preselected distance from said fitting with said lower and upper sealing means disconnected from said body lower end portion and said fitting, respectively.

5. The rotary union as recited in claim 4, wherein:
   said outer side wall of said body is threaded at said body lower end portion; and
   said lower sealing means includes an elastomeric bushing seated in a cap having a threaded inner wall for engaging the threaded lower end portion of said body to releasably connect said bushing and said cap to said lower end portion of said body.

6. The rotary union as recited in claim 5, wherein said elastomeric bushing has an annular base portion and an annular body portion extending therefrom which is split to define a plurality of fingers operable to expand when said cap is disconnected from said body lower end portion to allow said connector element and said another connector element to pass therethrough.

7. The rotary union as recited in claim 6, wherein said elastomeric bushing is made of rubber.

8. The rotary union as recited in claim 6, wherein said connector element is a hollow pipe.

9. The rotary union as recited in claim 4, wherein:
   said fitting has an outer wall threaded at the upper end portion thereof; and
   said upper sealing means includes an annular elastomeric bushing seated in a cap having a threaded inner wall for engaging the threaded upper end portion of said fitting to releasably connect said bushing and said cap to said fitting.

10. The rotary union as recited in claim 9, wherein said annular elastomeric bushing is made of rubber.

11. The rotary union as recited in claim 9, wherein:
    said fitting has a generally annular configuration and a lower end portion opposite said upper end portion of said fitting; and
    said stationary body is counterbored at its upper end portion to receive said lower end portion of said fitting.

12. The rotary union as recited in claim 11, wherein:
    said fitting has a cylindrical sidewall extending between said fitting lower and upper end portions and a circumferential groove formed in and extending around said cylindrical sidewall; and
    retaining means is secured to said body at said body upper end portion and extends into said circumferential groove in said fitting sidewall for rotatably securing said fitting within said body counterbore.

13. The rotary union as recited in claim 12, wherein said retaining means includes a pair of arcuate plates.

14. The rotary union as recited in claim 12, wherein:
    an O-ring groove located between said fitting lower end portion and said circumferential groove is formed in and extends around said cylindrical sidewall of said fitting; and
    an O-ring is positioned within said O-ring groove for providing a water tight seal between said sidewall of said fitting and said counterbore of said body.

* * * * *